United States Patent [19]

Hall, II et al.

[11] Patent Number: 5,840,343

[45] Date of Patent: *Nov. 24, 1998

[54] ROOM TEMPERATURE STERILANT FOR MEDICAL DEVICES

[75] Inventors: Robert T. Hall, II, Welch; Bradley K. Onstad, Deephaven; Daniel B. Carlsen, St. Louis Park, all of Minn.

[73] Assignee: Minntech Corporation, Minneapolis, Minn.

[ * ] Notice: The term of this patent shall not extend beyond the expiration date of Pat. No. 5,589,507.

[21] Appl. No.: 838,339

[22] Filed: Apr. 8, 1997

Related U.S. Application Data

[63] Continuation of Ser. No. 565,995, Dec. 1, 1995, abandoned.

[51] Int. Cl.$^6$ ........................... A01N 59/00; A01N 37/02; A01N 37/16

[52] U.S. Cl. ........................... 424/616; 424/613; 514/529; 514/546; 514/557; 514/558; 422/7; 422/12; 422/28; 422/29

[58] Field of Search ..................................... 514/529, 546, 514/557, 558; 424/613, 616; 422/29, 12, 7, 28

[56] References Cited

U.S. PATENT DOCUMENTS

| | | | |
|---|---|---|---|
| 5,344,652 | 9/1994 | Hall, II et al. | 424/405 |
| 5,545,343 | 8/1996 | Brougham et al. | 514/557 |
| 5,589,507 | 12/1996 | Hall, II et al. | 514/557 |
| 5,616,616 | 4/1997 | Hall, II et al. | 514/557 |

FOREIGN PATENT DOCUMENTS

| | | |
|---|---|---|
| 0231632 | 8/1987 | European Pat. Off. . |
| 0269435 | 6/1988 | European Pat. Off. . |
| 387974 | 6/1973 | U.S.S.R. . |
| 9524388 | 9/1995 | WIPO . |

OTHER PUBLICATIONS

D. Kozarov, et al., "Disinfectant Effect of Performic Acid," J. of Hygiene, Epidemiology, Microbiology and Immunology, 19.3, 1975, pp. 389–392 (Czech. Oslovak Medical Press, Prague).

*Primary Examiner*—John Pak
*Attorney, Agent, or Firm*—Cushman Darby & Cushman IP Group of Pillsbury Madison & Sutro, LLP

[57] ABSTRACT

Provided is an anti-microbial composition containing an ester of formic acid, an oxidizer, performic acid and water. Also provided is a premix for making the anti-microbial composition having two parts. One part contains the ester of formic acid and a second part contains the oxidizer. Another method is provided for making the anti-microbial composition in which the ester of formic acid is combined with the oxidizer and water. A further method is provided for sterilizing medical devices, including dialyzer filter modules, wherein the anti-microbial composition is capable of a 1:1 to a 1:12 dilution with water.

15 Claims, 6 Drawing Sheets

ROOM TEMPERATURE STERILANT FOR MEDICAL DEVICES

This is a continuation of application Ser. No. 08/565,995, filed on Dec. 1, 1995, which was abandoned upon the filing hereof.

BACKGROUND OF THE INVENTION

1. Field of the Invention

The invention relates to a room temperature anti-microbial composition which includes an ester of formic acid, an oxidizer, performic acid, and water, a premix for making the anti-microbial composition, a method for producing the anti-microbial composition, and a method for sterilizing medical devices utilizing the anti-microbial composition.

2. Background of Related Art

Conventional methods of sterilizing medical devices have significant disadvantages. For example, the steam autoclave works well, but many instruments are sensitive to the high pressure and temperature required to achieve sterility. Ethylene oxide requires long exposure times in a vacuum, even longer aeration times, and the gas is highly toxic. Glutaraldehyde is a suspected carcinogen and can be corrosive to certain materials. In the field of medical devices which come in contact with a patient's blood stream, care must be taken to sterilize or reprocess these devices with biocompatible anti-microbial compositions.

This is particularly true concerning catheters and blood filters such as dialyzers. Many of the aforementioned sterilizing techniques leave residues on the surfaces of the sterilized device which are toxic to the human body and may cause severe adverse patient reactions, such as skin rashes, hemolysis, and the like. Furthermore, if the dialyzer is to be reprocessed for reuse, it is particularly important that the anti-microbial composition be an effective biocide while remaining biocompatible because any residual anti-microbial composition may elute from the dialyzer into the bloodstream of the dialyzed patient, again causing severe adverse patient reaction, which may exacerbate the condition of the patient already in renal failure.

SUMMARY OF THE INVENTION

An object of the present invention is to provide an easy to use room temperature anti-microbial composition.

A further object of the present invention is to provide an anti-microbial composition for sterilizing medical devices which overcomes the disadvantages of known methods of sterilizing medical devices.

The invention relates to an anti-microbial composition having improved anti-corrosive properties comprising an ester of formic acid, an oxidizer, performic acid and water.

A preferred embodiment of the invention relates to an anti-microbial composition having improved anti-corrosive properties comprising about 0.01 to about 10 wt. % of an ester of formic acid selected from the group consisting of ethyl formate, methyl formate, propyl formate, or mixtures thereof, about 0.01 to about 10 wt. % of an oxidizer, about 0.001 to about 5 wt. % of performic acid, and up to about 99.98% water.

The invention also relates to a premix for making the anti-microbial composition comprising two parts. One part comprises the ester of formic acid and a second part comprises the oxidizer.

The invention further relates to a method making the anti-microbial composition comprising the steps of combining the premix.

The invention also relates to a method of producing the anti-microbial composition comprising the steps of combining an ester of formic acid with an oxidizer and water.

The invention further relates to a method of sterilizing surfaces comprising contacting the surface with an anti-microbial composition diluted to a working concentration, the anti-microbial composition comprising from about 0.01 to about 10 wt. % of an ester of formic acid selected from the group consisting of ethyl formate, methyl formate, propyl formate, or mixtures thereof, about 0.01 to about 10 wt. % of an oxidizer, about 0.001 to about 5 wt. % of performic acid, and up to about 99.98% water.

A further embodiment of the invention relates to a method of sterilizing blood filters, such as dialyzers used as artificial kidneys, comprising contacting the dialyzers the anti-microbial composition comprising from about 0.01 to about 10 wt. % of an ester of formic acid selected from the group consisting of ethyl formate, methyl formate, propyl formate, or mixtures thereof, about 0.01 to about 10 wt. % of an oxidizer, about 0.001 to about 5 wt. % of performic acid, and up to about 99.98% water. The anti-microbial composition can be diluted to a working concentration by dilution from 1:1 to 1:12 with water.

DETAILED DESCRIPTION OF THE PREFERRED EMBODIMENTS

Figure 1:
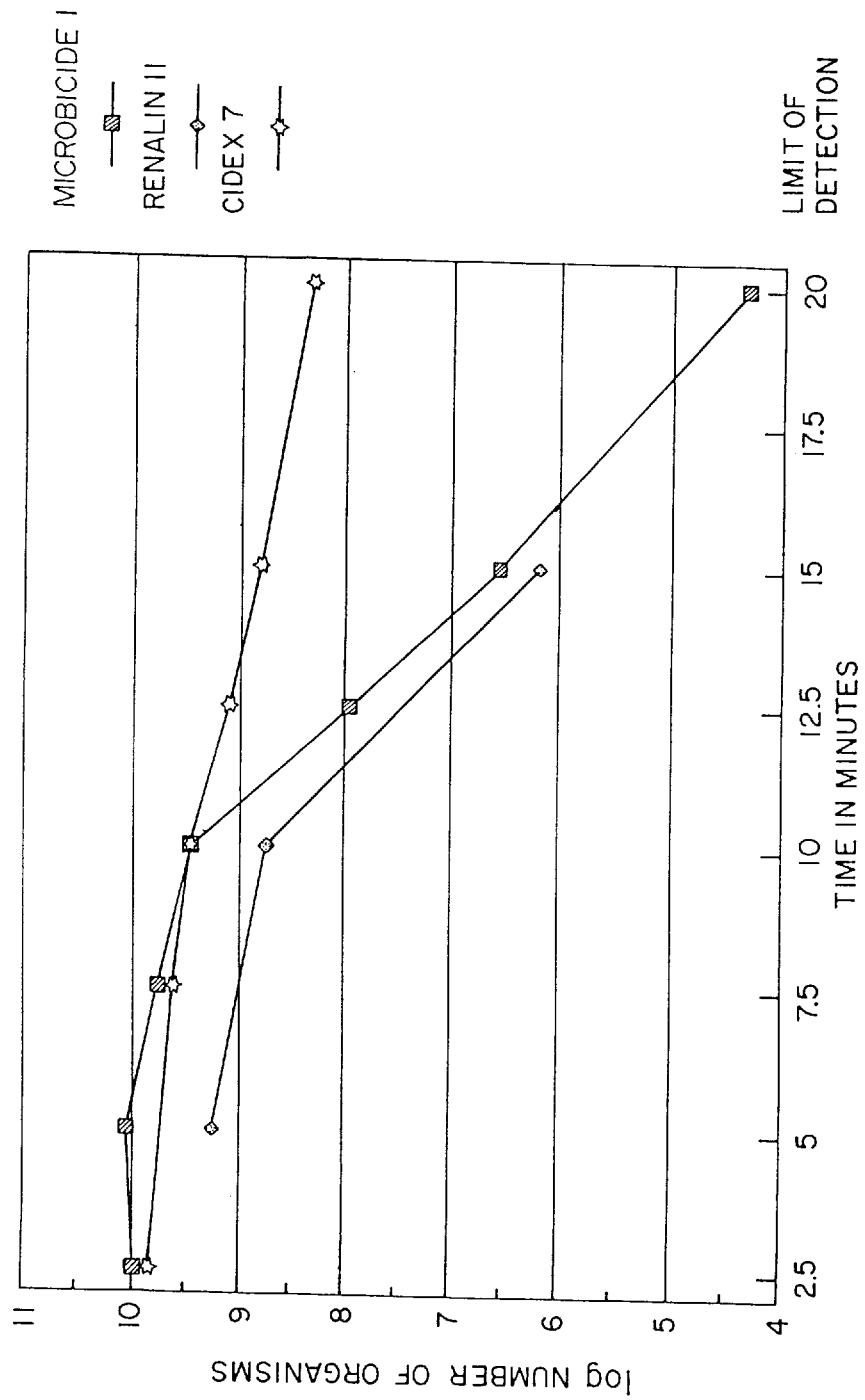
FIG. 1. illustrates the sporicidal effects of the anti-microbial composition according to the invention compared to two conventional anti-microbial compositions.

The invention relates to an anti-microbial composition having improved anti-corrosive properties comprising an ester of formic acid, an oxidizer, performic acid and water.

Preferably, the anti-microbial composition comprises about 0.01 to about 10 wt. % of the ester of formic acid, about 0.01 to about 10 wt. % of an oxidizer, about 0.001 to about 5 wt. % of performic acid, and up to about 99.98 wt. % water. More preferably, the anti-microbial composition comprises about 2 to about 8 wt. % of the ester of formic acid, about 1 to 10 wt. % of an oxidizer, about 0.001 to about 1 wt. % of performic acid, and up to about 97 wt. % of water.

Preferably, the ester of formic acid is an ester of ethyl formate, methyl formate, propyl formate, or mixtures thereof. More preferably, the ester of formic acid is ethyl formate.

The oxidizer can be any oxidizer that is compatible with a performic acid based anti-microbial composition. Examples of such oxidizers include nonorganic oxidizing substances such as, hydrogen peroxide, sodium percarbonate, sodium periodate, sodium persulfate, ammonium persulfate, sodium perborate, sodium peroxide, calcium peroxide, silver (II) oxide, ozone, and chlorine dioxide. The oxidizers also include organic oxidizing substances, for example, diacyl peroxides, such as benzoyl peroxide, ketone peroxides, such as 2, 4-pentanedione peroxide, peroxydicarbonates, such as diisopropyl peroxydicarbonate, peroxyesters, such as t-butylperoxy maleic acid, dialkyl peroxides, such as dicumyl peroxide, hydroperoxides, such as t-butyl hydroperoxide, and peroxyketals, such as 2,2-di (t-butyl peroxy) butane.

Preferably, the oxidizer is hydrogen peroxide. More preferably, the oxidizer is urea hydrogen peroxide.

A preferred anti-microbial composition comprises ethyl formate in an amount of about 3 to about 6 wt. %, urea hydrogen peroxide in an amount of about 1 to about 8 wt. %, and about 0.001 to about 1 wt. % of performic acid.

The anti-microbial composition can also contain additives, such as, corrosion inhibitors and stabilizers.

Examples of corrosion inhibitors are 1,2,3-Benzotriazole, azimidobenzene and benzene azimide (collectively, COBRATEC 99™, PMC Specialties Group, Inc.) and the sodium hydroxide reaction products of an aliphatic alcohol and phosphorous pentoxide (VICTAWET™ 35B, Akzo Chemicals, Inc., Chicago, Ill). The corrosion inhibiting properties of VICTAWET™ 35B are disclosed in PCT/US90/01862, entitled "Anticorrosive Microbicide."

The stabilizers include those that stabilize the anti-microbial composition over time, and those that increase the concentration of performic acid, as well as other stabilizers.

The anti-microbial composition can be made in a concentrated form, dry or liquid, to be diluted with water before using.

Purifying the water is not required. When hard tap water is used, surprisingly, the concentration of performic acid in the anti-microbial composition is less likely to decrease or will increase at the expense of the oxidizer, compared to deionized water. This is a significant advantage, because tap water is more readily available and is less expensive than purified or deionized water. In particular, hard water containing calcium acts in this manner.

The invention also relates to a premix for making the anti-microbial composition comprising a first part comprising an ester of formic acid, and a second part comprising the oxidizer. The oxidizer and ester of formic acid include those described above. The anti-microbial composition can be formed by combining the first and second parts with water.

Preferably, the first part comprises an ester of ethyl formate, methyl formate, propyl formate, or mixtures thereof, and the second part comprises hydrogen peroxide.

Preferably, the amount of the ester of formic acid in the first part and the amount of oxidizer are such that when combined with water the resulting anti-microbial composition comprises about 0.01 to about 10 wt. % of the ester of formic acid, about 0.01 to about 10 wt. % of the oxidizer, about 0.001 to about 5 wt. % of performic acid, and up to about 99.98% water.

Each part of the premix can be in a dry or liquid form. For example, one or both parts of the premix can be diluted with water. Alternatively, one part can contain all of the required water so that when the other part is added no further water is required, or sufficient water is present in both parts so that when both parts are combined no further water is required.

The premix can also contain the above described additives in either or both of the parts.

The invention further relates to a method of making the anti-microbial composition comprising the steps of combing both parts of the pre-mix. If the pre-mix does not contain the required amount of water, water and the first and second parts can be mixed in any order. Preferably, the anti-microbial composition comprises from about 2 to 5 wt. % ethyl formate, from about 3 to 8 wt. % hydrogen peroxide and from about 87 to 95 wt. % water.

Another embodiment of the invention relates to a method of producing the anti-microbial composition comprising the steps of combining the ester of formic acid with the oxidizer and water.

Preferably, sufficient amounts of water, ester of formic acid, and oxidizer are combined so that the resulting anti-microbial composition comprises about 0.01 to about 10 wt. % of the ester of formic acid, about 0.01 to about 10 wt. % of the oxidizer, about 0.001 to about 5 wt. % of performic acid, and up to about 99.98 wt. % water.

The anti-microbial composition can be used in place of conventional microbicides. The following is a partial list of uses for the anti-microbial composition. The uses of the anti-microbial composition is in no way intended to be limited to this list.

The anti-microbial composition can be used to sterilize the surfaces of medical devices and eating utensils. The anti-microbial composition can also be used to cleanse skin because it is non-toxic and non-irritating to the skin. For example, the anti-microbial composition can be used to cleanse patient pre-operative sites and medical personnel skin, such as hands and arms in presurgical scrubbing.

The anti-microbial composition is particularly useful for reprocessing used catheters which are sensitive to conventional anti-microbial compositions. Preferably, when the anti-microbial composition is used to reprocess used catheters, the anti-microbial composition contains "VICTAWET™ 35b." is believed that the VICTAWET™ acts as a lubricant for the mechanical pump during reprocessing. The reprocessing method disclosed in U.S. Pat. Nos. 4,721,123 and 5,310,524 are incorporated herein.

The anti-microbial composition is also particularly useful for sterilizing filter modules containing filter membranes in various forms, such as hollow fibers. Sterilization of filter modules using the anti-microbial composition of the present invention is particularly useful for reprocessing hollow fiber membrane dialyzers because not only are the dialyzers rendered microbe-free but the anti-microbial composition also removes residual proteinaceous blood components. Hollow fiber filter cartridges sterilized using the anti-microbial composition are suitable for re-use in a medical dialysis setting, such as for artificial kidney.

The invention will be further described by the following non-limiting examples.

EXAMPLE 1

Three tests were performed on samples of an anti-microbial composition according to the invention made by combining 3.8 to 4% by weight of ethyl formate, 4% urea hydrogen peroxide, and the balance water, which will hereinafter be referred to as "Microbicide 1" for notation purposes only. Performic acid was generated in an amount of about 0.001 to about 0.1 wt. %.

The anti-microbial composition was compared to two known microbicides, CIDEX™ 7 (Johnson and Johnson, Medical) and 1% RENALIN® II (Minntech Corporation, published in PCT/US92/05877).

In the first test, the sporicidal and bactericidal activity of each anti-microbial composition was tested by placing ~1×10¹⁰ *Bacillus subtilis* spores into 10 ml of anti-microbial composition in a closed, but not sealed, test tube at room temperature (about 20° C.). At exposure times of 2.5, 5, 7.5, 10, 12.5, 15, 17.5 and 20 minutes, 1 ml was removed and placed in a neutralizer solution to stop the sterilant action. The neutralizer solution comprised 1% Bacto-peptone (Difco), 1% sodium thiosulfate, and 0.025% catalase. The surviving spores were then serially diluted and plated to count.

FIG. 1 illustrates the rate of kill by plotting the log number of surviving organisms vs. exposure time. FIG. 1 illustrates that the Microbicide 1 curve closely fits the 1% Renalin II curve. Therefore, the anti-microbial composition of the present invention exhibits anti-microbial effects equal to or greater than 1% RENALIN® II. FIG. 1 also illustrates that Microbicide 1 exhibits significantly greater anti-microbial effects than CIDEX™ 7, on the order of four logs, after 20 minutes.

The above test was repeated, except using methyl formate, butyl formate, or propyl formate in place of ethyl formate in the same molar concentration. After 20 minutes, $5 \times 10^4$ bacteria were observed and after 60 minutes no bacterial were observed in the methyl formate solution. After 20 minutes, no bacterial were observed and after 60 minutes $6 \times 10^4$ bacterial were observed in the propyl formate solution. The propyl formate solution was retested and no bacteria was observed after 20 and 60 minutes. Therefore, the bacteria observed after 60 minutes in the propyl formate solution was a procedural error. After 20 minutes, $4.3 \times 10^7$ bacterial were observed and after 60 minutes $3.3 \times 10^6$ bacteria were observed in the butyl formate solution.

Figure 2:
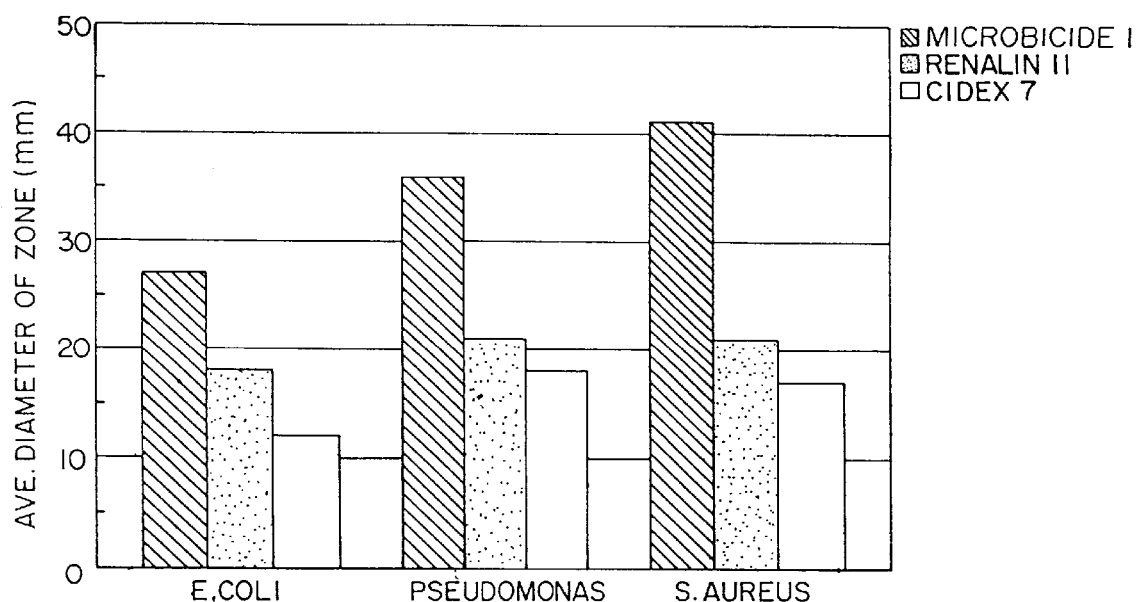
FIG. 2. illustrates the bactericidal effects of the anti-microbial composition according to the invention compared to two conventional anti-microbial compositions.

A second text was performed by coating a petri dish (Falcon Corp.), containing an agar made using tryptic soy (Difco Labs), with either *Staphylococcus aureus*, *Pseudomonas aeruginosa*, or *E. coli*. After the plates were dry, three wells were punched into the agar and filled to the top with either Microbicide 1, RENALIN® II or CIDEX™ 7. The plates were then incubated for 48 hours at 37° C. The area around the well where no bacterial grew (zone of inhibition) was then measured and graphed. FIG. 2 illustrates the results. The zones where no bacterial grew were significantly larger for Microbicide 1 than they were for RENALIN® II and CIDEX™ 7. This data illustrates that anti-microbial composition of the present invention kills significantly more organisms than either of RENALIN® II or CIDEX™ 7, and that it kills *Pseudomonas spp*. This is of considerable importance because CIDEX™ 7 has been reported to have difficulty in killing *Pseudomonas spp*. This test is similar to the test used for determining the relative effectiveness and/or resistance of microorganisms to antibiotics.

A third test was performed in which an AOAC 966.04 (1990) sporicidal test done on *Clostridium sporogenes* using suture loops as the carrier. The results are summarized in Table 1. All tests were run for 5½ hours at 20° C. unless stated otherwise.

TABLE 1

| Description: | Results (negatives/#samples): |
| --- | --- |
| Microbicide 1 | 49/50 |
| ½ concentration Microbicide 1 | 19/20 |

TABLE 1-continued

| Description: | Results (negatives/#samples): |
| --- | --- |
| Microbicide 1 pH 7 | 20/20 |
| Microbicide 1 in synthetic hard water | 20/20 |
| Microbicide 1 in tap water | 20/20 |
| Microbicide 1 at 3½ hours exposure | 37/40 |
| Microbicide 1 2½ hours exposure | 20/20 |
| Microbicide 1 (double)[1] 12 min. exp. | 19/20 |
| Microbicide 1 (double)[1] 20 min. exp. | 20/20 |
| Microbicide 1 (double)[2] 12 min. exp. | 17/20 |
| Microbicide 1 (double)[2] 20 min. exp. | 20/20 |
| Microbicide 1 (double)[2] 30 min. exp. | 20/20 |

*A tube is considered negative if no growth is observed after 21 days of incubating, heat shocking at 80° C. for 20 minutes and then incubating again for another 72 hours.
[1]Double the amount of urea hydrogen peroxide and ethyl formate, 2 wt. % COBRATEC 99 ™ 50° C.
[2]Double the amount of urea hydrogen peroxide and ethyl formate, 50° C.

A difference of <5 is not statistically significant.

EXAMPLE 2

The corrosive effects of the composition of the present invention were tested using the same formulation, Microbicide 1, as used in Example 1, except where noted.

In the first test, the corrosive effects of the present invention and 1% RENALIN® II on chrome plated Kerr dental mirrors. The formulation of the present invention tested was the same as in Example 1 except that it did not include COBRATEC 99™ and was adjusted to a pH 7 using 0.1N NaOH. The pH of the composition of the present invention before adjusting was 3.8. The mirrors were soaked at room temperature (about 20° C.) in a closed container (screw on lid) for a two week period in about 120 ml of Microbicide 1 or 1% RENALIN® II. The solutions were changed daily by pouring out the used liquid and refilling with fresh.

This test was an appearance type of inspection process rather than a quantitative evaluation. Upon examination after the two week period, the mirrors soaked in Microbicide 1 had a significantly better appearance than the mirrors soaked in 1% RENALIN® II. RENALIN® II etched away the chrome layer, exposing the brass underneath. The brass was beginning to corrode which turned the 1% RENALIN® II solution blue. The Microbicide 1 only slightly dulled the appearance of the chrome plating.

In the second test, the corrosion effects of Microbicide 1 and 3% RENALIN® II on a naval brass coupons (approximately 12.3 gms) were tested. The composition of the present invention was tested as in Example 1 except where noted.

Before testing, the brass coupons were cleaned to remove oils, dirt, etc., by placing the coupons in a glass tray containing acetone and sonicating for about 5 minutes, removing the coupons with forceps, rinsing with deionized water, and then air drying. The coupons were then weighed (Wt1).

The method used to test the corrosion effects is outlined in the ASTM G1-90, (1992) Vol. 3.02, pp. 35–38. Each naval brass coupon was soaked in about 120 ml of test solution for a time period of 24 hours in a plastic specimen cup.

The rate of corrosion was measured using the mass lost during the 24 hour soak period as follows. The naval brass coupons were removed from the test liquids, rinsed thoroughly with deionized water, dried and weighed (Wt2). The corrosion products were then removed from the tested coupons. All of the tested coupons and one blank coupon were submerged in 10% sulfuric acid for 2 minutes while sonicating. The coupons were then rinsed thoroughly with deionized water, air dried and weighed (Wt3). Each coupon was placed on the back of a modified test tube rack in between two glass slides on each side of the coupon. A weighted SCOTCH BRITE™ pad (3M Corp.) was wrapped around each coupon and the coupon was rubbed 10 times each way with the pad, allowing the weight of the pad to be the only downward force exerted on the coupons. Both sides of the coupons were rubbed with the pad. All of the coupons were then placed in 10% sulfuric acid and sonicated for 2 minutes. The coupons were then rinsed, air dried and weighed (Wt4). The coupons were immersed in sulfuric acid and rubbed with the pad as described above until the weight loss of the tested coupons was almost equal to the amount lost by the blank coupon. The weight loss of the tested coupons will not be equal to the amount lost by the blank coupon, but they will usually be within about 0.001 g of each other. Each weight was measured after air drying as (Wt″).

The corrosion rate was calculated using the following formula:

$$\text{corrosion rate (mm/yr)} = (K \times W)/(A \times T \times D)$$

where:

A=area of coupon in $cm^2$ to nearest 0.1 $cm^2$ (std=28.7 $cm^2$)

K=a constant ($8.76 \times 10^4$)

T=time of exposure in hours to the nearest 0.25 hours.

W=the mass lost in g, to the nearest 1 mg. corrected for the mass lost during cleaning (initial weight–Wt″ of treated coupon) minus (Initial weight–Wt″ of blank coupon).

D=density in $g/cm^3$ of material tested (naval brass c-464- 8.41 $g/cm^3$).

Figure 3:
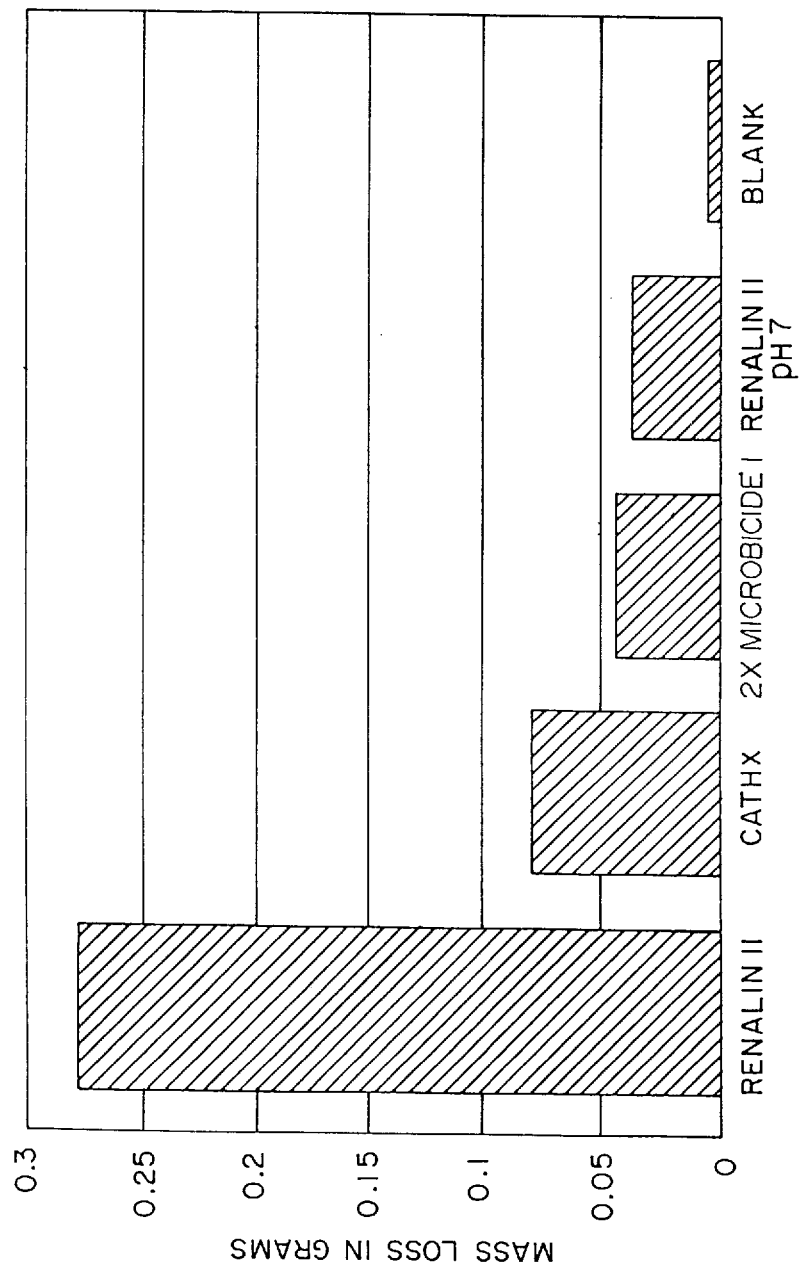
FIG. 3. illustrates the net mass loss of brass after 24 hours of exposure as measured in Example 2.

The results are shown in Table 2 and FIG. 3.

TABLE 2

| SUBSTANCE TESTED: | CORROSION RATE: |
|---|---|
| Microbicide 1 pH 7, 2x concentrate | .57 mm/yr |
| Microbicide 1 pH 7 | 1.40 mm/yr |
| Microbicide 1 pH 7, w/.1% "Cobratec 99 ™ | .061 mm/yr |
| Microbicide 1 w/.1% "Cobratec 99 ™ | .094 mm/yr |
| Microbicide 1 w/.17% "Cobratec 99 ™ | .035 mm/yr |
| Microbicide 1 w/.1% "Victawet ™ 35B | .77 mm/yr |
| Microbicide 1 w/.1% "Victawet ™ 58 | .34 mm/yr |
| Microbicide 1 pH 7, w/.1% sodium nitrite | 1.26 mm/yr |
| Microbicide 1 pH 7.8, w/.1% sodium nitrite | 1.24 mm/yr |
| $Cath_x$ | 1.10 mm/yr |
| 3% Renalin ® II | 4.13 mm/yr |

The addition of small amounts of Cobratec 99™ significantly reduced the corrosion rate of brass.

In the third test, the corrosion effects of Microbicide 1 and 1% Renalin® on dental burrs and carbon steel scalpel blades was tested. Microbicide 1 and 1% Renalin® II, and the test procedures, were the same as used in the first test of Example 2, except where noted. Microbicide 1 made the burrs tarnish in 24 hours, but the addition of the Cobratec 99™ (0.2%) almost eliminated this problem. To compare, 1% Renalin™ etched the burr away. The scalpel blades showed no signs of corrosion from Microbicide 1, with or without Cobratec™. 1% Renalin performed equally well as Microbicide 1. However, deionized water (deionized using a mixed bed deionizing system) rusted the blades.

EXAMPLE 3

The stability of Microbicide 1 was tested. Formulas 599-81-18 through 599-81-20 used a 1 quart bottle (Twin City Bottle), with vented caps, which was filled with the test solution and the lid screwed on. The 1 quart bottles were stored in a closed cabinet at room temperature (about 20° C.). All of the other formulas used 30 gm glass vials, which were filled with the test solution and the lids screwed on. The vials were stored on an open bench top under fluorescent light at room temperature (about 20° C.). The formulas with a "T" at the end signifies that the test solution was stored at 50° C. instead of 20° C.

The test solution, length of time tested and the test results are shown in Table 3. The synthetic hard water used was made by the method described in Official Methods of Analysis, Germicidal and Detergent Sanitizing Action of Disinfectants (Final Action) 960.09 page 139 "Synthetic Hard Water" (Section E).

Figure 4:
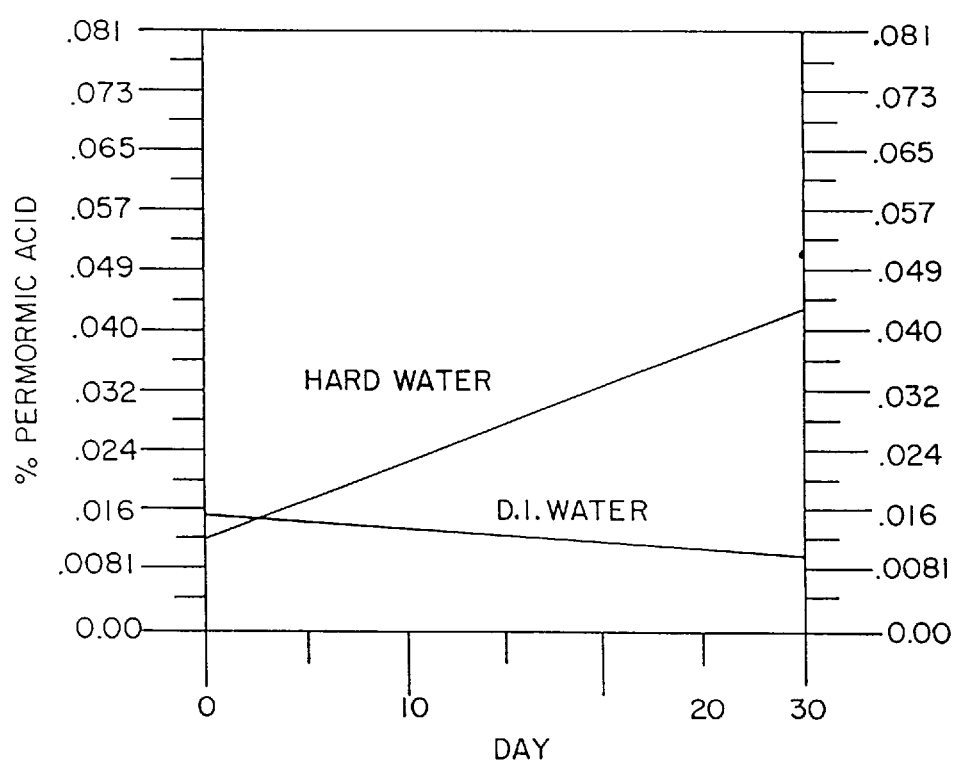
FIG. 4. illustrates the concentration of performic acid in hard and deionized water over time as measured in Example 3.
Figure 5:
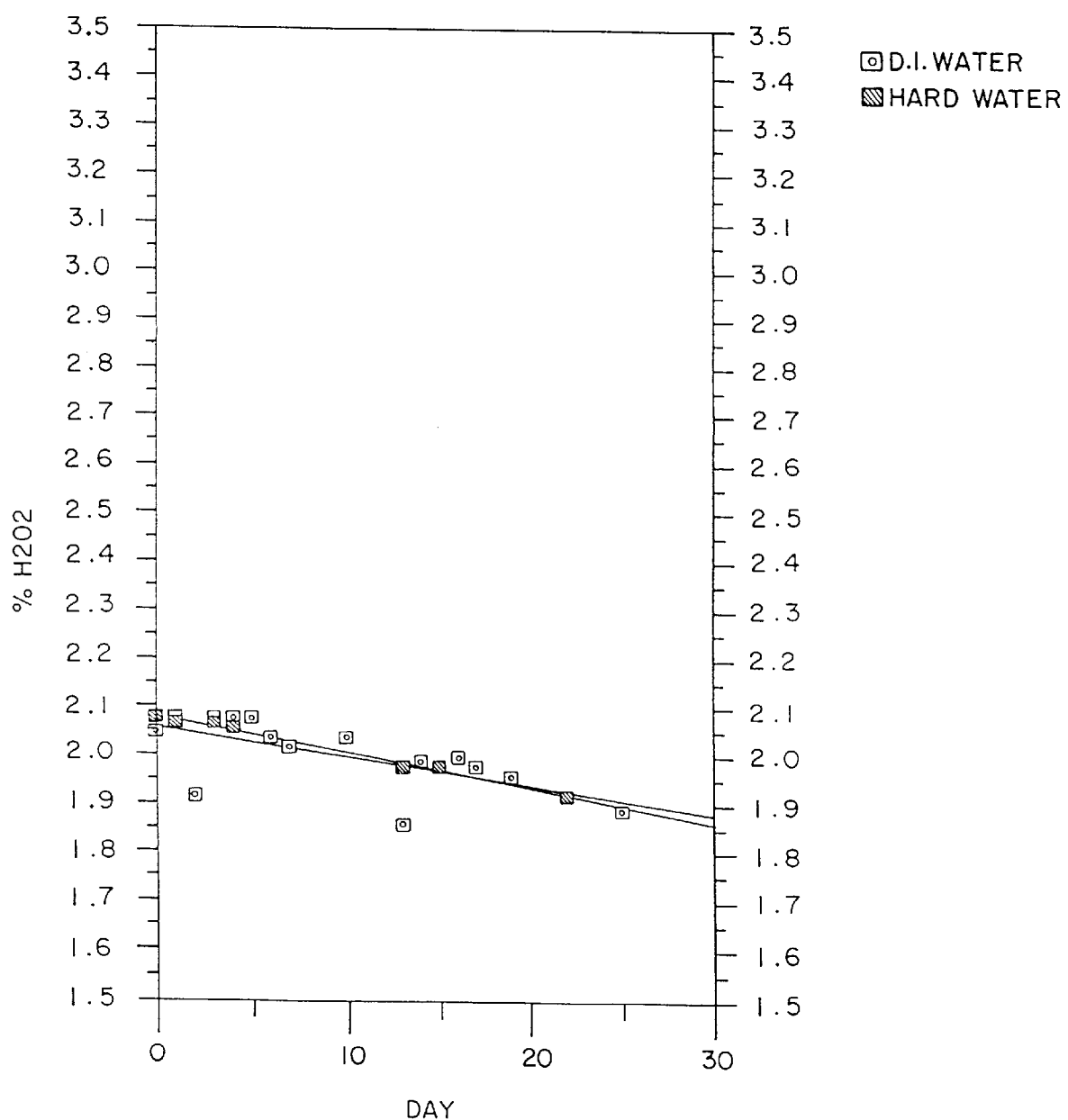
FIG. 5. illustrates the concentration of hydrogen peroxide in hard and deionized water over time as measured in Example 3.
Figure 6:
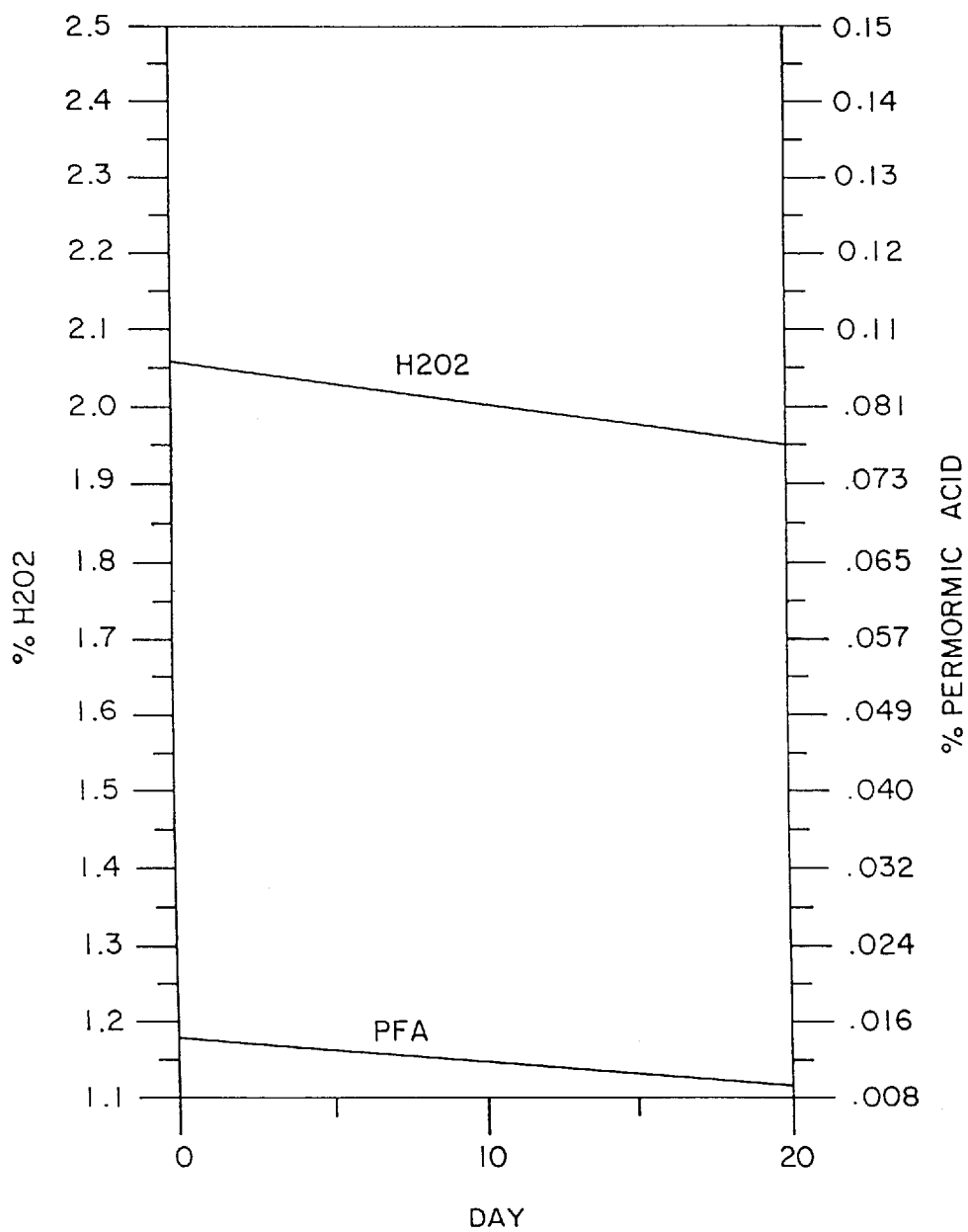
FIG. 6. illustrates the stability of hydrogen peroxide and performic acid in deionized water over time as measured in Example 3.

The results are also shown in FIGS. 4–6. FIG. 4 illustrates the concentration of performic acid in hard and deionized water over time. FIG. 5 illustrates the concentration of hydrogen peroxide in hard and deionized water over time. FIG. 6 illustrates the stability of hydrogen peroxide and performic acid in deionized water over time.

EXAMPLE 4

The anti-microbial composition of the present invention for dialyzer reprocessing was tested. The initial amount of components in the anti-microbial composition of the present invention for sterilizing/reprocessing can be in the range from about 1 to 10 wt. % of an ester of formic acid selected from the group consisting of ethyl formate, methyl formate, propyl formate and mixtures thereof; from about 1 to 10 wt. % of an oxidizer; from about 0.001 to 0.1 wt. % performic acid; and up to about 99.98 wt. % water. Preferably, the initial amount of the ester of formic acid is about 2 to about 7 wt. % and the oxidizer is from about 3 to 9 wt. % with the remainder water. More preferably, the initial amount of the ester of formic acid is about 2 to 4 wt. % and the oxidizer is about 4 to 8 wt. % and most preferably, the ester of formic acid is about 2.2 wt. % and the oxidizer is about 7 wt. % (hereinafter abbreviated as "Microbicide 2" for notation purposes only).

For dialyzer sterilizing/reprocessing, Microbicide 2 can be diluted from about 1:1 to about 1:12, and preferably between 1:5 and 1:6, with water. It is to be understood that in order to remain an effective anti-microbial agent, the anti-microbial composition for dialyzer reprocessing is diluted such that the oxidizer final working concentration is between about 0.1 to about 2.0 wt. %.

The dialyzer hollow fiber filter units Primus® 1000 high flux polysulfone dialyzers by Renal Systems®, Division of Minntech Corporation) were first steam sterilized prior to any reprocessing. Dialyzers were reprocessed or sterilized using Microbicide 2 were compared to dialyzers reprocessed using another anti-microbial composition of hydrogen peroxide, acetic acid and peracetic acid, namely RENALIN® (Minntech Corporation). Dialyzers were attached to an automated dialyzer reprocessor, namely RENATRON® (Minntech Corporation), wherein the anti-microbial composition tested was diluted per RENATRON® protocol, about 1:5, with water. The diluted anti-microbial composition was then cycled through the dialyzer filter so that the diluted anti-microbial composition flows through the hollow fibers in the dialyzer. Performance parameters for dialyzers reprocessed with Microbicide 2 and RENALIN® were compared.

In particular, the following performance measurements were taken on dialyzers reprocessed with either Microbicide 2 or RENALIN®. Specifically, water permeability, or flux, measured as ml/min·cm²·mmHg and Na⁺ clearance, as an estimate for plasma urea clearance measured as ml/min, were performed on reprocessed dialyzers. Baseline pretreatment measurements were taken on the steam sterilized dialyzers prior to any reprocessing. Performance measurements were then taken on reprocessed dialyzers after 10 treatments, or reprocessing cycles on the RENATRON®, and after 20 treatments. Also, after 20 treatments, the reprocessed dialyzers were evaluated for BSA rejection, as an indicator for albumin rejection during dialysis. The following table summarizes the results.

TABLE 3

| | Number of Exposures to Anti-Microbial Composition | | |
|---|---|---|---|
| | 0 | 10 | 20 |
| Microbicide 2[1] | | | |
| Flux | 23.95 +/− 2.33 | 31.88 +/− 4.03 | 30.05 +/− 3.15 |
| Clearance | 171.35 +/− 3.81 | 168.67 +/− 4.08 | 163.27 +/− 4.74 |
| BSA rejection | | | 99.90 +/− 0.04 |

TABLE 3-continued

| | Number of Exposures to Anti-Microbial Composition | | |
|---|---|---|---|
| | 0 | 10 | 20 |
| RENALIN® | | | |
| Flux | 23.90 | 35.90 | 28.20 |
| | 26.00 | 28.60 | 35.50 |
| Clearance | 178.70 | 161.47 | 171.24 |
| | 158.90 | 178.10 | 177.17 |
| BSA rejection | | | 99.89 |
| | | | 99.88 |

[1]Six steam sterilized dialyzers were reprocessed using Microbicide 2 which was diluted about 1:5 with water during reprocessing in the RENATRON®.
[2]Two steam sterilized dialyzers were reprocessed using RENALIN® so that about a 3.5% RENALIN® solution in water passed through the dialyzer during reprocessing in the RENATRON®.

Comparison between the performance measurements taken from the dialyzers reprocessed using Microbicide 2 and those taken from the dialyzers using a conventional reprocessing anti-microbial composition indicate that the performance of Microbicide 2 reprocessed dialyzers is substantially similar to the performance of the conventionally reprocessed dialyzers.

TABLE 3

| | | FORMULATION | | | WATER TYPE | | | TITRATION #1 | | |
|---|---|---|---|---|---|---|---|---|---|---|
| FORMULA # | DATE | EF, g | U/P, g | 50% H2O2 | DI, g | TAP, g | HARD, g | DATE | % H2O2 | % PFA |
| 599-56-1 | 10/7/93 | 0.44 | 1.2 | | 20 | | | 10/7/93 | 2.09 | 0.0089 |
| 599-56-3 | 10/8/93 | 0.44 | 1.2 | | 20 | | | 10/8/93 | 2.11 | 0.0073 |
| 599-56-4 | 10/11/93 | 0.44 | 1.2 | | 20 | | | 10/11/93 | 2.08 | 0.0065 |
| 599-56-5 | 10/11/93 | 0.44 | 1.2 | | 20 | | | 10/11/93 | 2.08 | 0.0154 |
| 599-56-6 | 10/12/93 | 0.44 | 1.2 | | 20 | | | 10/12/93 | 1.91 | 0.0113 |
| 599-56-7 | 10/15/93 | 0.44 | 1.2 | | 20 | | | 10/15/93 | 2.08 | 0.0154 |
| 599-57-11 | 10/8/93 | 0.88 | 1.2 | | 20 | | | 10/8/93 | 2.11 | 0.0105 |
| 599-57-12 | 10/8/93 | 0.44 | 1.2 | | 20 | | | 10/8/93 | 3.83 | 0.0089 |
| 599-64-13-H | 10/25/93 | 0.44 | 1.2 | | | | 20 500 PPM Ca | 10/26/93 | 2.3 | 0.0211 |
| 599-64-14-H | 10/25/93 | 0.52 | 1.2 | | | | 20 500 PPM Ca | 10/26/93 | 2.11 | 0.0130 |
| 599-65-15-T | 10/26/93 | 0.44 | 1.2 | | | 20 | | 10/26/93 | 2.06 | 0.0122 |
| 599-65-16-T | 10/26/93 | 0.44 | 1.2 | | | 20 | | 10/26/93 | 2.07 | 0.0105 |
| 599-65-17-T | 10/26/93 | 0.88 | 2.4 | | | 20 | | 10/26/93 | 2.86 | 0.0105 |
| 599-65-18-T | 10/26/93 | 0.88 | 2.4 | | | 20 | | 10/26/93 | 3.9 | 0.0178 |
| 599-65-19-T | 10/26/93 | 0.22 | 1.2 | | | 20 | | 10/26/93 | 2.08 | 0.0049 |
| 599-65-20-T | 10/26/93 | 0.22 | 1.2 | | | 20 | | 10/27/93 | 2.06 | 0.0162 |
| 599-66-13 | 10/29/93 | 0.22 | 0.6 | | 20 | | | 10/29/93 | 1.08 | 0.0057 |
| 599-66-14 | 10/29/93 | 0.22 | 0.6 | | 20 | | | 10/29/93 | 1.07 | 0.0008 |
| 599-66-15 | 10/29/93 | 0.22 | 0.6 | | 20 | | | 10/29/93 | 1.08 | 0.0081 |
| 599-66-16 | 10/29/93 | 0.22 | 0.6 | | 20 | | | 10/29/93 | 1.09 | 0.0041 |
| 599-80-1 | 11/18/93 | 0.44 | 1.2 | | 20 | | | 11/19/93 | 2.06 | 0.0113 |
| 599-80-2 | 11/18/93 | 0.44 | 1.2 | | 20 | | | 11/19/93 | 2.08 | 0.0122 |
| 599-80-3 | 11/18/93 | 0.44 | 1.2 | | 20 | | | 11/19/93 | 2.07 | 0.0105 |
| S99-80-4 | 11/18/93 | 0.44 | 1.2 | | 20 | | | 11/19/93 | 2.08 | 0.0081 |
| 599-80-5 | 11/18/93 | 0.44 | 1.2 | | | | 20 500 PPM | | | |
| 599-80-6 | 11/18/93 | 0.44 | 1.2 | | | | 20 500 PPM | 11/19/93 | 2.02 | 0.0251 |
| 599-80-7 | 11/18/93 | 0.44 | 1.2 | | | | 20 500 PPM | 11/19/93 | 2.09 | 0.0150 |
| 599-80-8 | 11/18/93 | 0.44 | 1.2 | | | | 20 500 PPM | 11/19/93 | 2.07 | 0.0154 |
| 599-80-9 | 11/18/93 | 0.44 | 1.2 | | | | 20 1000 PPM | 11/19/93 | 2.07 | 0.0113 |
| 599-80-10 | 11/18/93 | 0.44 | 1.2 | | | | 20 1000 PPM | 11/19/93 | 1.95 | 0.0113 |
| 599-81-11-Ca | 11/19/93 | 0.44 | 1.2 | | | | 20 500 PPM CaCl1 | 11/22/93 | 2.05 | 0.0138 |
| 599-81-42-Ca | 11/19/93 | 0.44 | 1.2 | | | | 20 500 PPM CaCl2 | 11/22/93 | 2.06 | 0.0186 |
| 599-81-13-Bi | 11/19/93 | 0.44 | 1.2 | | | | 20 .22g/L BICARB | 11/22/93 | 2.06 | 0.0097 |
| 599-81-14-Bi | 11/19/93 | 0.44 | 1.2 | | | | .22g/L BICARB | 11/22/93 | 2.02 | 0.0122 |
| 599-81-15-Bc | 11/19/93 | 0.44 | 1.2 | | | | .22g/L BICARB | 11/22/93 | 2.06 | 0.0178 |
| 599-81-16-Bc | 11/19/93 | 0.44 | 1.2 | | | | .22g/L BICARB | 11/22/93 | 2.05 | 0.0178 |
| 599-81-17 | 11/19/93 | 0.44 | 1.2 | | 1 quart | | | 11/22/93 | 2.11 | 0.0130 |
| 599-81-18 | 11/19/93 | 0.44 | 1.2 | | 1 quart | | | 11/22/93 | 2.14 | 1.2231 |
| 599-81-19 | 11/19/93 | 1.32 | 3.6 | | 1 quart | | | 11/22/93 | 5.28 | 0.0502 |
| 599-81-20 | 11/19/93 | 1.32 | 3.6 | | 1 quart | | | 11/22/93 | 5.26 | 0.0292 |

TABLE 3-continued

| Formula # | Date | | | | | | Date | | |
|---|---|---|---|---|---|---|---|---|---|
| 599-83-21 | 11/23/93 | 1.8 | 4.8 | | 20 g | | 11/23/93 | 6.72 | 0.0340 |
| 599-83-22 | 11/23/93 | 1.8 | 4.8 | | 20 g | | 11/23/93 | 6.67 | 0.0292 |
| 599-83-23 | 11/23/93 | 1.8 | 4.8 | | | 20 500 PPM | 11/23/93 | 5.88 | 0.0446 |
| 599-83-24 | 11/23/93 | 1.8 | 4.8 | | | 20 500 PPM | 11/23/93 | 6.75 | 0.0470 |
| 599-83-25 | 11/23/93 | 1.8 | 4.8 | | | 20 1000 PPM | 11/23/93 | 6.7 | 0.0446 |
| 599-83-26 | 11/23/93 | 1.8 | 4.8 | | | 20 1000 PPM | 11/23/93 | 6.79 | 0.0494 |
| 599-83-27 | 11/23/93 | 1.8 | 4.8 | | | 20 1000 PPM Ca | 11/23/93 | 6.72 | 0.0462 |
| 599-83-28 | 11/23/93 | 1.8 | 4.8 | | | 20 1000 PPM Ca | 11/23/93 | 6.73 | 0.0494 |
| 599-83-29 | 11/23/93 | 1.8 | 4.8 | | 20 g | | 11/23/93 | 6.72 | 0.0429 |
| 599-83-30 | 11/23/93 | 0 | 4.8 | | 20 g | | 11/23/93 | 6.9 | 0.0089 |
| 599-83-31 | 11/23/93 | 1.8 | 0 | | 20 g | | 11/23/93 | 0.004 | 0.0032 |
| 534-28-1 | 2/15/94 | 0.44 | 1.2 | | 20 g | | 2/15/94 | mixing time and temperature | |
| 534-29-1 | 2/15/94 | 0.44 | | 0.8 | 18.76 | | 2/17/94 | 2.12 | 0.0073 |
| 534-29-1T | 2/15/94 | 0.44 | | 0.8 | 18.76 | | 2/17/94 | 2.12 | 0.0073 |
| 534-29-2 | 2/15/94 | 0.88 | | 0.8 | 18.32 | | 2/17/94 | 2.25 | 0.0275 |
| 534-29-2T | 2/15/94 | 0.88 | | 0.8 | 18.32 | | 2/17/94 | 2.25 | 0.0275 |
| 534-29-3 | 2/15/94 | 0.44 | | 1.6 | 17.96 | | 2/17/94 | 4.2 | 0.0219 |
| 534-29-3T | 2/15/94 | 0.44 | | 1.6 | 17.96 | | 2/17/94 | 4.2 | 0.0219 |
| 534-29-4 | 2/15/94 | 0.88 | | 1.6 | 17.52 | | 2/17/94 | 4.32 | 0.0259 |
| 534-29-4T | 2/15/94 | 0.88 | | 1.6 | 17.52 | | 2/17/94 | 4.32 | 0.0259 |
| 534-29-5 | 2/15/94 | 1.76 | | 1.6 | 16.64 | | 2/17/94 | 4.5 | 0.0243 |
| 534-29-5T | 2/15/94 | 1.76 | | 1.6 | 16.64 | | 2/17/94 | 4.5. | 0.0243 |
| 534-29-6 | 2/15/94 | 0.44 | | 3.2 | 16.36 | | 2/17/94 | 8.26 | 0.0284 |
| 534-29-6T | 2/15/94 | 0.44 | | 3.2 | 16.36 | | 2/17/94 | 8.26 | 0.0284 |
| 534-29-7 | 2/15/94 | 0.88 | | 3.2 | 15.92 | | 2/17/94 | 8.35 | 0.0251 |
| 534-29-7F | 2/15/94 | 0.88 | | 3.2 | 15.92 | | 2/17/94 | 8.35 | 0.0251 |
| 534-29-8 | 2/15/94 | 1.76 | | 3.2 | 15.04 | | 2/17/94 | 8.64 | 0.0267 |
| 534-29-8T | 2/15/94 | 1.76 | | 3.2 | 15.04 | | 2/17/94 | 8.64 | 0.0267 |
| 534-29-9 | 2/15/94 | 1.76 | | 3.2 | 15.04 | | 2/17/94 | 8.6 | 0.0535 |
| 534-29-9T | 2/15/94 | 1.76 | | 3.2 | 15.04 | | 2/17/94 | 8.6 | 0.0535 |
| 534-29-10 | 2/15/94 | 3.52 | | 3.2. | 13.28 | | 2/17/94 | 9.63 | 0.0599 |
| 534-29-10T | 2/15/94 | 3.52 | | 3.2 | 13.28 | | 2/17/94 | 9.63 | 0.0599 |
| 534-29-11 | 2/15/94 | 8 | | 52 | 0 | | 2/17/94 | 44.9 | 0.2349 |
| 534-29-11T | 2/15/94 | 8 | | 52 | 0 | | 2/17/94 | 44.9 | 0.2349 |
| 534-29-12 | 2/15/94 | 6 | | 54 | 0 | | 2/17/94 | 46.8 | 0.5249 |
| 534-29-12T | 2/15/94 | 6 | | 54 | 0 | | 2/17/94 | 46.8 | 0.5249 |
| 534-29-13 | 2/15/94 | 4 | | 56 | 0 | | 2/17/94 | 46.1 | 0.2584 |
| 534-29-13T | 2/15/94 | 4 | | 56 | 0 | | 2/17/94 | 46.1 | 0.2584 |
| 534-29-14 | 2/15/94 | 2 | | 58 | 0 | | 2/17/94 | 49.8 | 0.1393 |
| 534-29-14T | 2/15/94 | 2 | | 58 | 0 | | 2/17/94 | 49.8 | 0.1393 |
| 534-29-15 | 2/15/94 | 10 | | 50 | 0 | | 2/17/94 | 45.6 | 0.4755 |
| 534-29-15T | 2/15/94 | 10 | | 50 | 0 | | 2/17/94 | 45.6 | 0.4755 |
| 534-29-16 | 2/15/94 | 1.76 | | 3.2 | 7.04 | 8 g 1000 PPM | 2/17/94 | 8.48 | 0.0275 |
| 534-29-16T | 2/15/94 | 1.76 | | 3.2 | 7.04 | 8 g 1000 PPM | 2/17/94 | 8.48 | 0.0275 |
| 524-29-17 | 2/15/94 | 1.76 | | 3.2 | 9.04 | 6 g 1000 PPM | 2/17/94 | 8.61 | 0.0543 |
| 524-29-17T | 2/15/94 | 1.76 | | 3.2 | 9.04 | 6 g 1000 PPM | 2/17/94 | 8.61 | 0.0543 |
| 524-29-18 | 2/15/94 | 1.76 | | 3.2 | 11.04 | 4 g 1000 PPM | 2/17/94 | 8.52 | 0.0697 |
| 524-29-18T | 2/15/94 | 1.76 | | 3.2 | 11.04 | 4 g 1000 PPM | 2/17/94 | 8.52 | 0.0697 |
| 524-29-19 | 2/15/94 | 1.76 | | 3.2 | 13.04 | 2 g 1000 PPM | 2/17/94 | 8.58 | 0.0680 |
| 524-29-19T | 2/15/94 | 1.76 | | 3.2 | 13.04 | 2 g 1000 PPM | 2/17/94 | 8.58 | 0.0680 |
| 529-29-20 | 2/15/94 | 1.76 | | 3.2 | 14.04 | 1 g 1000 PPM | 2/17/94 | 8.57 | 0.0680 |
| 529-29-20T | 2/15/94 | 1.76 | | 3.2 | 14.04 | 1 g 1000 PPM | 2/17/94 | 8.57 | 0.0770 |
| 529-29-21 | 2/15/94 | 1.76 | | 3.2 | 6.8 | 10 g 1000 PPM | 2/17/94 | 6.98 | 0.0770 |
| 529-29-21T | 2/15/94 | 1.76 | | 3.2 | 6.8 | 10 g 1000 PPM | 2/17/94 | 6.98 | 0.0648 |
| 529-29-22 | 2/15/94 | 0 | | 3.2 | 16.8 | | 2/17/94 | 8.14 | 0.0648 |
| 529-29-22T | 2/15/94 | 0 | | 3.2 | 16.8 | | 2/17/94 | 8.14 | 0.0356 |
| 529-29-23 | 2/15/94 | 0.44 | | 0.8 | 18.72 | .04 g COBRATEC 99 | 2/17/94 | 2.18 | 0.0356 |
| 529-29-23T | 2/15/94 | 0.44 | | 0.8 | 18.72 | .04 g COBRATEC 99 | 2/17/94 | 2.18 | 0.0186 |
| 529-29-24 | 2/15/94 | 0.44 | | 1.2 | 20 | | 2/17/94 | 2.09 | 0.0186 |
| 529-29-24T | 2/15/94 | 0.44 | | 1.2 | 20 | | 2/17/94 | 2.09 | 0.0154 |
| 529-29-25 | 2/15/94 | 0.44 | | 1.2 | 20 | | 2/17/94 | 2.09 | 0.0170 |
| 529-29-25T | 2/15/94 | 0.44 | | 1.2 | 20 | | 2/17/94 | 2.09 | 0.0170 |
| 529-29-26 | 2/15/94 | 0 | | 3.2 | 16.8 | | 2/17/94 | 8.66 | 0.0348 |
| 529-29-26T | 2/15/94 | 0 | | 3.2 | 16.8 | | 2/17/94 | 8.66 | 0.348 |

| | TITRATION #2 | | | TITRATION #3 | | | TITRATION #4 | | |
|---|---|---|---|---|---|---|---|---|---|
| FORMULA # | DATE | % H2O2 | % PFA | DATE | % H2O2 | % PFA | DATE | % H2O2 | % PFA |
| 599-56-1 | 10/8/93 | 2.06 | 0.0154 | 10/11/93 | 2.07 | 0.0146 | 10/12/93 | 2.08 | 0.0162 |
| 599-56-3 | 10/11/93 | 2.09 | 0.0122 | 10/11/93 | 2.1 | 0.0122 | 10/12/93 | 2.1 | 0.0154 |
| 599-56-4 | 10/12/93 | 2.08 | 0.0138 | 10/14/93 | 2.07 | 0.0162 | 10/25/93 | 1.99 | 0.0041 |
| 599-56-5 | 10/12/93 | 2.07 | 0.0113 | 10/14/93 | 2.07 | 0.0138 | 10/15/93 | 2.06 | 0.0186 |
| 599-56-6 | 10/14/93 | 1.92 | 0.0130 | 10/25/93 | 1.86 | 0.0122 | 2/15/94 | 1.49 | 0.0105 |
| 599-56-7 | 10/25/93 | 2.04 | 0.0219 | 2/15/94 | 1.64 | 0.0146 | | | |
| 599-57-11 | 10/8/93 | 2.15 | 0.0122 | 10/12/93 | 2.08 | 0.0162 | 10/14/93 | 2.04 | 0.0130 |
| 599-57-12 | 10/8/93 | 3.84 | 0.0073 | 10/12/93 | 3.78 | 0.0122 | 10/14/93 | 3.75 | 0.0105 |
| 599-64-13-H | 10/26/93 | 2.09 | 0.0518 | 10/26/93 | 2.03 | 0.0154 | 10/26/93 | 2.04 | 0.0138 |

TABLE 3-continued

| | | | | | | | | | |
|---|---|---|---|---|---|---|---|---|---|
| 599-64-14-H | 11/2/93 | 2.03 | 0.0186 | 11/18/93 | 1.84 | 0.0194 | 2/15/94 | 1.41 | 0.0535 |
| 599-65-15-T | 10/27/93 | 2.03 | 0.0122 | 11/2/93 | 1.99 | 0.0049 | 11/18/93 | 1.85 | 0.0032 |
| 599-65-16-T | 11/2/93 | 1.99 | 0.0049 | 11/18/93 | 1.85 | 0.0073 | 2/15/94 | 1.42 | 0.0186 |
| 599-65-17-T | 10/27/93 | 3.81 | 0.0259 | 11/2/93 | 3.6 | 0.0113 | 11/18/93 | 3.13 | 0.0146 |
| 599-65-18-T | 11/2/93 | 3.63 | 0.0170 | 11/18/93 | 31.5 | 0.0122 | 2/15/94 | 2.25 | 0.0105 |
| 599-65-19-T | 10/26/93 | 2.06 | 0.0097 | 2/15/94 | 1.72 | 0.0211 | | | |
| 599-65-20-T | 2/15/94 | 1.67 | 0.0041 | | | | | | |
| 599-66-13 | 11/2/93 | 1.08 | 0.0081 | 2/15/94 | 0.93 | 0.0348 | | | |
| 599-66-14 | 11/2/93 | 1.08 | 0.0081 | 2/15/94 | 0.94 | 0.0235 | | | |
| 599-66-15 | 11/2/93 | 1.09 | 0.0041 | 2/15/94 | 0.96 | 0.0203 | | | |
| 599-66-16 | 11/2/93 | 1.09 | 0.0057 | 2/15/94 | 0.94 | 0.0251 | | | |
| 599-80-1 | 11/22/93 | 2.04 | 0.0073 | 2/15/94 | 1.59 | 0.0105 | | | |
| 599-80-2 | 11/22/93 | 2.07 | 0.0162 | 2/15/94 | 1.65 | 0.0113 | | | |
| 599-80-3 | 11/22/93 | 2.05 | 0.0097 | 2/15/94 | 1.64 | 0.0243 | | | |
| 599-80-4 | 11/22/93 | 2.06 | 0.0154 | 2/15/94 | 1.61 | 0.0170 | | | |
| 599-80-6 | 11/22/93 | 1.99 | 0.0146 | 2/15/94 | 1.56 | 0.0834 | | | |
| 599-80-7 | 11/22/93 | 2.06 | 0.1539 | 2/1S/94 | 1.56 | | | | |
| 599-80-8 | 11/22/93 | 2.04 | 0.0170 | 2/15/94 | 1.54 | 0.0656 | | | |
| 599-80-9 | 11/22/93 | 2.03 | 0.0154 | 2/15/94 | 1.4 | 0.0810 | | | |
| 599-80-10 | 11/22/93 | 1.94 | 0.0178 | 2/14/94 | 1.39 | 0.0640 | | | |
| 599-81-11-Ca | 2/14/94 | 1.6 | 0.0397 | | | | | | |
| 599-81-42-Ca | 2/14/94 | 1.58 | 0.0413 | | | | | | |
| 599-81-13-Bi | 2/14/94 | 1.64 | 0.0130 | | | | | | |
| 599-81-14-Bi | 2/14/94 | 1.66 | 0.0130 | | | | | | |
| 599-81-15-Bc | 2/14/94 | 106 | 0.0664 | | | | | | |
| 599-81-17 | 2/14/94 | 1.69 | 0.0105 | | | | | | |
| 599-81-18 | 2/14/93 | 1.5 | 0.0243 | | | | | | |
| 599-81-19 | 2/14/93 | 3.13 | 0.1134 | 2/15/94 | 3.15 | 0.0284 | | | |
| 599-81-20 | 2/14/93 | 3.22 | 0.0486 | 2/15/94 | 3.2 | 0.0275 | 2/15/94 | 3.16 | 0.0308 |
| 599-81-21 | 12/3/93 | 5.58 | 0.0208 | 2/14/94 | 3.79 | 0.0365 | | | |
| 599-83-22 | 12/3/93 | 5.38 | 0.0373 | 2/14/94 | 3.66 | 0.0340 | | | |
| 599-83-23 | 12/3/93 | 4.97 | 0.0624 | 2/14/94 | 3.26 | 0.0421 | | | |
| 599-83-24 | 12/3/93 | 5.49 | 0.0632 | 2/14/94 | 3.69 | 0.0365 | | | |
| 599-83-25 | 12/3/93 | | 0.0923 | 2/14/94 | 3.39 | 0.0421 | | | |
| 599-83-26 | 12/3/93 | 5.41 | 0.0899 | 2/14/94 | 3.51 | 0.0713 | | | |
| 599-83-27 | 12/3/93 | 5.63 | 0.0729 | 2/14/94 | 3.74 | 0.0421 | | | |
| 599-83-28 | 12/14/93 | 3.74 | 0.0365 | | | | | | |
| 599-83-29 | 12/14/93 | 3.76 | 0.0348 | | | | | | |

| | TITRATION #5 | | | TITRATION #6 | | | TITRATION #7 | | |
|---|---|---|---|---|---|---|---|---|---|
| FORMULA # | DATE | % H2O2 | % PFA | DATE | % H2O2 | % PFA | DATE | % H2O2 | % PFA |
| 599-56-1 | 10/14/93 | 2.04 | 0.0138 | 10/15/93 | 2.02 | 0.0154 | 10/25/93 | 1.96 | 0.0073 |
| 599-56-3 | 10/14/93 | 2.08 | 0.0138 | 10/25/93 | 1.99 | 0.0081 | 10/27/93 | 1.98 | 0.0146 |
| 599-56-4 | 10/27/93 | 2 | 0.0073 | 2/15/94 | 1.52 | 0.0186 | | | |
| 599-56-5 | 10/25/93 | 1.98 | 0.0275 | 10/25/93 | 1.97 | 0.0267 | 10/27/93 | 1.98 | 0.0454 |
| 599-57-11 | 10/25/93 | 1.86 | 0.0130 | 2/15/94 | 0.95 | 0.0235 | | | |
| 599-57-12 | 10/25/93 | 3.59 | 0.0113 | 2/15/94 | 1.36 | 0.0194 | | | |
| 599-64-13-H | 10/27/93 | 2.04 | 0.0178 | 11/2/93 | 2 | 0.0178 | 11/18/93 | 1.82 | 0.0203 |
| 599-65-15-T | 2/15/94 | 1.43 | 0.0065 | | | | | | |
| 599-65-17-T | 2/15/94 | 2.24 | 0.0089 | | | | | | |

| | TITRATION #8 | | | TITRATION #9 | | | TITRATION #10 | | |
|---|---|---|---|---|---|---|---|---|---|
| FORMULA # | DATE | % H2O2 | % PFA | DATE | % H2O2 | % PFA | DATE | % H2O2 | % PFA |
| 599-56-1 | 10/27/93 | 1.94 | 0.0081 | 11/2/93 | 1.89 | 0.0145 | 11/8/93 | 1.78 | 0.0065 |
| 599-56-3 | 2/15/94 | 1.44 | 0.0316 | | | | | | |
| 599-56-5 | 10/29/93 | 1.95 | 0.0356 | 11/2/93 | 1.92 | 0.0267 | 11/18/93 | 1.81 | 0.0292 |
| 599-64-13-H | 2/15/94 | 1.38 | 0.0332 | | | | | | |

| | TITRATION #11 | | |
|---|---|---|---|
| FORMULA # | DATE | % H2O2 | % PFA |
| 599-56-5 | 2/15/94 | 1.4 | 0.0243 |

While the invention has been described in detail and with reference to specific embodiments thereof, it will be apparent to one of ordinary skill in the art that various changes and modifications can be made therein without departing from the spirit and scope thereof.

What is claimed is:

1. A method of sterilizing a filter module with an anti-microbial composition comprising contacting the filter module with the anti-microbial composition comprising from about 0.01 to about 10.0 wt. % of an ester of formic acid; from about 0.01 to about 10.0 wt. % of an oxidizer; from about 0.001 to about 5.0 wt. % performic acid and up to about 99.98 wt. % water.

2. A method of sterilizing a filter module according to claim 1, wherein the ester of formic acid is selected from the group consisting of ethyl formate, methyl formate, propyl formate, and mixtures thereof.

3. A method of sterilizing a filter module according to claim 1, wherein the oxidizer is hydrogen peroxide.

4. A method of sterilizing a filter module according to claim 2, wherein the ester of formic acid is ethyl formate.

5. A method of sterilizing a filter module according to claim 2, wherein the ester of formic acid is ethyl formate and the oxidizer is hydrogen peroxide.

6. A method of sterilizing a filter module according to claim 5, wherein ethyl formate is in an amount from about 0.02 to about 5.0 wt. %; hydrogen peroxide is in an amount from about 0.02 to about 5.0 wt. %; performic acid is in an amount from about 0.001 to about 1.0 wt. %; and up to about 99.98 wt. % water.

7. A method of sterilizing a filter module with an anti-microbial composition comprising contacting the filter module with the anti-microbial composition provided by combining about 2.2 wt. % ester of formic acid, about 7.0 wt. % oxidizer, and about 90.8 wt. % water.

8. A method of sterilizing a filter module according to claim 7, wherein the ester of formic acid is selected from the group consisting of ethyl formate, methyl formate, propyl formate, and mixtures thereof.

9. A method of sterilizing a filter module according to claim 7, wherein the oxidizer is hydrogen peroxide.

10. A method of sterilizing a filter module according to claim 8, wherein the ester of formic acid is ethyl formate.

11. A method of sterilizing a filter module according to claim 8, wherein the ester of formic acid is ethyl formate and the oxidizer is hydrogen peroxide.

12. A method of sterilizing a filter module according to claim 11, wherein the anti-microbial composition is capable of dilution with water such that the oxidizer is present in an amount between about 0.1 to about 2.0 wt. %.

13. A method of sterilizing a filter module with an anti-microbial composition comprising:

(a) providing an anti-microbial composition comprising from about 0.01 to about 10.0 wt. % of an ester of formic acid; from about 0.01 to about 10.0 wt. % of an oxidizer; from about 0.001 to about 5.0 wt. % performic acid and up to about 99.98 wt. % water;

(b) diluting the anti-microbial composition from about 1:1 to about 1:12 with water; and (c) contacting the filter module with a diluted anti-microbial composition from step (b).

14. A method of sterilizing a filter module with an anti-microbial composition according to claim 13, wherein the diluted anti-microbial composition from step (b) is characterized as including the oxidizer in an amount between about 0.1 to about 2.0 wt. %.

15. A method of sterilizing a filter module comprising contacting the filter module with an anti-microbial composition, the anti-microbial composition made by combining a sufficient amount of an ester of formic acid, an oxidizer and water to provide from about 0.01 to about 10.0 wt. % of the ester of formic acid, from about 0.01 to about 10.0 wt. % of the oxidizer, from about 0.001 to about 5.0 wt. % of performic acid, and up to about 99.98 wt. % of water; and wherein the anti-microbial composition is diluted from about 1:1 to about 1:12 with water.

* * * * *

UNITED STATES PATENT AND TRADEMARK OFFICE
CERTIFICATE OF CORRECTION

PATENT NO.  : 5,840,343

DATED       : November 24, 1998

INVENTOR(S): Hall, et. al.

It is certified that error appears in the above identified patent and that said Letters Patent are hereby corrected as shown below:

Column 4, line 2, delete "combing" and substitute --combining-- therefor.
Column 4, line 23, delete "is in no way" and substitute --are in no way-- therefor.
Column 5, line 26, delete "bacterial" and substitute --bacteria-- therefor.
Column 5, line 27, delete "bacterial" and substitute --bacteria-- therefor.
Column 5, line 28, delete "bacterial" and substitute --bacteria-- therefor.
Column 5, line 35, delete "text" and substitute --test-- therefor.
Column 5, line 42, delete "bacterial" and substitute --bacteria-- therefor.
Column 5, line 44, delete "bacterial" and substitute --bacteria-- therefor.

UNITED STATES PATENT AND TRADEMARK OFFICE
CERTIFICATE OF CORRECTION

PATENT NO. : 5,840,343
DATED : November 24, 1998
INVENTOR(S): Hall, et. al.

It is certified that error appears in the above identified patent and that said Letters Patent are hereby corrected as shown below:

Column 8, line 52, delete "Primus®" and substitute --(Primus®-- therefor.
Column 10, line 6, delete "RENALIN®" and substitute -- RENALIN®$^2$-- therefor.
Column 10, Table 3, column %PFA, line 27, delete "0.0150" and substitute --0.0130-- therefor.
Column 11, Table 3, group TITRATION #1, column FORMULATION Formula #1, line 27, delete "534-29-7F" and substitute --534-29-7T-- therefor.
Column 13, Table 3-continued, group TITRATION #2, column FORMULA #, line 30, delete "599-81-21" and substitute --599-83-21-- therefor.
Column 13, Table 3-continued, group TITRATION #2, column % PFA, line 30, delete "0.0208" and substitute --0.0308-- therefor.
Column 14, Table 3-continued, group TITRATION #9, column % PFA line 1, delete "0.0145" and substitute --0.0146-- therefor.

Signed and Sealed this

Sixteenth Day of November, 1999

Attest:

Attesting Officer

Q. TODD DICKINSON

Acting Commissioner of Patents and Trademarks